United States Patent [19]

Wawretschek et al.

[11] 4,061,741

[45] Dec. 6, 1977

[54] PHYSIOLOGICAL SUBSTANCES FOR INTENSIFYING THE PHARMACOLOGICAL EFFECT OF DRUGS

[75] Inventors: Wolfgang Wawretschek; Lothar Wawretschek, both of Munich, Germany

[73] Assignee: Firma Servomed Arzei GmbH & Co. Pharma KG, Munich, Germany

[21] Appl. No.: 562,736

[22] Filed: Mar. 27, 1975

[30] Foreign Application Priority Data

Apr. 1, 1974  Germany ............................ 2415740

[51] Int. Cl.$^2$ ................. A61K 31/625; A61K 31/505
[52] U.S. Cl. ..................................... 424/232; 424/251
[58] Field of Search ............................ 424/1, 251, 232

[56] References Cited

U.S. PATENT DOCUMENTS

| 3,105,077 | 9/1963 | Muller et al. ........................ 424/251 |
| 3,544,684 | 12/1970 | Scherm ................................ 424/251 |

FOREIGN PATENT DOCUMENTS

| 2,131,946 | 12/1972 | Germany ............................ 260/251 |
| 108,537 | 9/1974 | Germany ............................ 260/251 |
| 7,455,813 | 5/1974 | Japan ................................... 260/251 |

OTHER PUBLICATIONS

Anisimov, Chemical Abstracts, vol. 68, No. 17, Apr. 22, 1968, p. 7387, Abstract No. 76645p.

Glebov et al., Chemical Abstracts, vol. 71, No. 11, Sept. 15, 1969, p. 205, Abstract No. 47947v.

Keppler et al., Chemical Abstracts, vol. 72, No. 13, Mar. 30, 1970, p. 229, Abstract No. 65142d.

Ekren et al., Nuclear Science Abstracts, vol. 28, No. 3, Aug. 15, 1973, p. 570, Abstract No. 6007.

Weast, ed., *Handbook of Chemistry and Physics*, 49th Edition, Chemical Rubber Co., Cleveland, Ohio, 1968, pp. C–589, 593.

Grove, ed., *Webster's Third New International Dictionary*, G. & C. Merriam Co., Springfield, Mass., 1965, pp. 1593, 2522.

*Primary Examiner*—Benjamin R. Padgett
*Assistant Examiner*—Christine M. Nucker
*Attorney, Agent, or Firm*—Pollock, Vande Sande & Priddy

[57] ABSTRACT

Composition comprising a medicament and orotic acid and/or physiologically compatible salt thereof, and/or uridin-5-monophosphate in an amount sufficient to increase the efficiency of the composition, methods of use and preparation of the compositions are provided.

41 Claims, No Drawings

PHYSIOLOGICAL SUBSTANCES FOR INTENSIFYING THE PHARMACOLOGICAL EFFECT OF DRUGS

The present invention relates to a means of reinforcing the pharmacological action of medicaments which exhibit an affinity for linking with blood proteins in vivo and in vitro.

It is known that to a greater or lesser degree, medicaments are in vivo bonded with serum proteins (see prizewinning paper "Progress in medicament research", Vol. 14, 1970). This bond diminishes the pharmacological efficacy of a substance, since only unbonded pharmaceuticals are effective. Both forms balance each other in accordance with the law of mass action. Thus, according to M. C. Meyer and D. E. Guttmann (J. Pharm. Sci. 57, 895 (1968)), for example salicilates are in vivo reversibly bonded to human albumen, i.e. are converted to a depot form. A lowering of the concentration of non-bonded (active) medicament by degradation, segregation, dispersion, etc., will lead to the dissolution of such protein-medicament complexes. This behaviour in the organism is surely desirable in the treatment of many illnesses and in some cases it may even be strived for the purpose of depot formation, such as for example in the case of some antibiotics and sulphonamides.

The degree of the bonding of a substance to serum proteins depends upon its specific association constant and its concentration. A medicament with a relatively high constant or applied in a relatively high concentration may displace another from its protein bond and therefore, under certain circumstances, suddenly relatively large quantities of this substance may be rendered pharmacologically active (Frimmer, "Biological bases of pharmacological actions", 1971; Ritschel, "Applied Biopharmacy", 1973). Thus, for example, in the presence of phenyl butazone, the cumarins are more intensely liberated from their bond, so that the tendency in patients to bleed during anticoagulant therapy is enhanced (Rechenberg, "Butazolidin", 1961).

Generally, the main disadvantage of the described bond with serum proteins resides in the fact that after the discontinuance of a treatment, relatively large quantities of a medicament may still remain in the system for some prolonged period of time. They may for example be released again when a further drug is administered, therefore undesirable side effects may possibly occur.

The controlled at least partial prevention or dissolution of such protein-medicament complexes would make it possible to dose substantially more accurately and avoid many of the intolerance described in the international literature.

It is therefore an object of the present invention to find a means which is capable of providing a controlled increase of that portion of the drug to be used which is not bonded to the serum albumen, i.e. which is along effective. In this way a measurable reinforcement of the pharmacological action can be obtained in other words a reduction in the quantities of active principle therein is possible. It is an object of the present invention to provide a means which is however inert with respect to the special target of the therapy, and which therefore, on the other hand, as an unspecific factor, has a reinforcing effect on drugs of varying orientation.

According to the invention, this object is achieved by use of orotic acid (1,2,3,6-tetrahydro-2,6-dioxo-4-pyrimidine-carboxylic acid) and/or a physiologically tolerable orotic acid salt.

In order to establish the bonding affinity of the drugs to blood proteins, it is possible for example to proceed as follows: human serum is incubated at 37° C and pH 7.3 to 7.4 with a radioactively marked drug (for example marked $C^{14}$) in a definite concentration per milliliter of serum for 60 minutes. 1 ml of this serum is then ultrafiltered at the same temperature, accompanied by agitation. (Filter permeability up to a molecular weight of approx. 10,000). The radioactivity contained in this ml is measured. The measured value, found multiplied by the concentration per ml used, and divided by 100, indicates the percentage of drug which is not bonded to protein. The same test is repeated but in the presence of non-radioactively marked orotic acid in a molar ratio to the marked drug of for example 1:1 or 1:2. The percentage of free drug is calculated similarly as described above. If the second measured value is higher than the first, then this is a measure of improved availability of the drug. This increased availability is confirmed in experiments with animals. If, in the presence of the medium, no more drug is found, as for example in the case of phenyl butazone, then also no reinforced pharmacological action can be detected in experiments with animals.

Preferably, the molar ratio of the quantities of orotic acid to the drug amounts to at least 1:1 and is preferably 2:1.

According to the invention, orotic acid can be used as a salt former with the drug itself or in admixture with the drug as free orotic acid, or as a specific salt of orotic acid.

Thus, the desired reinforcement of action of L- and D-propoxyphene can according to the invention easily be achieved by forming the corresponding orotic acid salts, or as in the case of metamizol, codeine phosphate, sodium salicylate, etc., by mixing therein the rapidly absorbable choline orotate.

What is decisive thereby is the rapid availability of sufficient quantities of orotic acid from such compounds in the serum.

Therefore, a mixture of the orotic acid salt of the drug, for example with choline orotate, in the molar ratio of 1:1 is particularly favourable.

Further advantages and features of the invention will become manifest from the ensuing description of examples of embodiments:

EXAMPLE 1

Dextropropoxyphene-HCl, dextropropolyphenorotate and dextropropoxyphene orotate + orotic acid (in the molar ratio 1:1) were tested on mice to determine their analgesic efficacy after oral administration following the "writhing" syndrome. The $ED_{50}$ was determined after 15 minutes, 30 minutes, 60 minutes and 180 minutes. The results are summarised in the following Table I:

Table I $ED_{50}$ in kg/kg of mouse (calculated with respect to the dextropropoxyphene-HCl); oral application, writhing syndrome, 800 NMRI mice, female 20 to 22 g

| | 15 min. | 30 min. | 60 min. | 180 min. |
|---|---|---|---|---|
| Dextropropoxyphene-HCl | | 80 | 74 | 160 |
| Dextropropoxyphene orotate | 45 | 71 | 74 | 118 |
| Dextropropoxyphene orotate | | | | |

Table I-continued $ED_{50}$ in kg/kg of mouse (calculated with respect to the dextropropoxyphene-HCl);
oral application, writhing syndrome, 800 NMRI mice, female 20 to 22 g

|  | 15 min. | 30 min. | 60 min. | 180 min. |
|---|---|---|---|---|
| + orotic acid (1:1) | 37 | 48 | 66 | 95 |

As can be seen from the Table, the orotic acid salt of dextropropoxyphene is already substantially more intensely effective as an analgesic than dextropropoxyphene-HCl by itself. An even better analgesic efficacy is achieved after the addition of orotic acid to dextropropoxyphene orotate in the molar ratio of 1:1.

EXAMPLE 2

The antitussive efficacy of laevopropoxyphene-HCl and laevopropoxyphene orotate was compared on guinea pigs, using the Turner cough test. The results are summarised in the following Table II:

Table II

% cough inhibition 30 minutes after oral application.
70 guinea pigs, 250 g; 7.5% citric acid aerosol for 10 minutes in the respired air.

|  | mg/kg | | | | | |
|---|---|---|---|---|---|---|
|  | 25 | 50 | 75 | 100 | 150 | 200 |
| Laevopropoxyphene-HCl | 0 | 8 | 0 | 11 | 0 | 9 |
| Laevopropoxyphene orotate | 6 | 31 | 47 | 56 | — | — |

It was revealed that in this test laevopropoxyphene-HCl exhibited no antitussive efficacy in the dosages tested. On the other hand, the laevopropoxyphene orotate revealed an outstanding antitussive efficacy.

According to the Gaussian Integral, from the values shown in the Table, the $ED_{50}$ can be calculated for: L-propoxyphene-HCl as being greater than 200 mg/kg of animal, l-propoxyphene orotate 79 ± 8 mg/kg of animal.

EXAMPLE 3

As with Example 2, the two substances laevopropoxyphene-HCl and laevopropoxyphene orotate were tested and compared with respect to their antitussive action. This time, however, intravenous applications were adopted. The results are summarised in the following Table III:

Table III

% cough inhibition; the figures in brackets represent mg propoxyphene-HCl in the l-propoxyphene orotate.
320 guinea pigs (350 g); intravenous application. 7.5% citric acid aerosol.

|  | 5 min. | 10 min. | 15 min. | 20 min. |
|---|---|---|---|---|
| Laevopropoxyphene-HCl |  |  |  |  |
| 2 mg/kg | 11 | 0 | 0 | — |
| 5 mg/kg | 24 | 0 | 0 | — |
| 7.5 mg/kg |  | subtoxic |  |  |
| Laevopropoxyphene orotate |  |  |  |  |
| 1 (0.758) mg/kg | 17.5 | 24 | 30 | 23 |
| 3 (2.27) mg/kg | 31.0 | 30 | 36 | 47 |
| 5 (3.79) mg/kg | 40.5 | 48 | 53 | 59 |
| 7.5 (5.69) mg/kg | 52.0 | 59 | 63 | 62 |

The superior efficacy of laevopropoxyphene orotate is obvious.

EXAMPLE 4

The antitussive efficacy of laevopropoxyphene-HCl, laevopropoxyphene orotate, laevopropoxyphene orotate + choline orotate (in the molar ratio 1:1) and of laevopropoxyphene-HCl + choline orotate (in the molar ratio 1:2) was tested and compared after oral application on guinea pigs using the Turner cough test. The results obtained are summarised in the following Table IV:

Table IV $ED_{50}$ in mg/kg of guinea pig. Values calculated with respect to l-propoxyphene-HCl.
280 guinea pigs (350 g); oral application.
7.5% citric acid aerosol.

|  | 1 hr. | 3 hr. |
|---|---|---|
| Laevorpopoxyphene-HCl | 250 mg/kg | 195 mg/kg |
| Laevopropoxyphene crotate | 103 mg/kg | 68 mg/kg |
| Laevopropoxyphene orotate + choline orotate (1:1) | 101 mg/kg | 47 mg/kg |
| Laevopropoxyphene-HCl + choline orotate (1:2) | 52 mg/kg | 45 mg/kg |

Both after 1 hour and also after 3 hours, a clear superiority of all orotic acid salts or mixtures in comparison with laevopropoxyphene-HCl was demonstrated. The test results show that there is a considerable increase in efficacy when choline orotate is used in mixture with laevopropoxyphene orotate in the molar ratio of 1:1. According to the invention, this effect can be substantially enhanced if, in the mixture of drug:orotic acid, the proportion of orotic acid is used in the form of choline orotate, which is substantially better resorbed (see Table IV, last line).

EXAMPLE 5

The analgesic efficacy of sodium salicylate, sodium salicylate + choline orotate in the molar ratio of 1:1 and sodium salicylate + choline orotate in the molar ratio of 1:2 was compared in the writhing test on mice and the $ED_{50}$ determined after 1 hour. The results obtained are summarised in the following Table V:

Table V $ED_{50}$ in mg/kg of mouse 60 minutes following oral application.
Writhing test.
260 CFI mice (18 – 20 g)

|  | 60 mins. |
|---|---|
| Sodium salicylate | 580 mg/kg |
| Sodium salicylate + cholineorotate (molar ratio 1:1) | 200 mg/kg |
| Sodium salicylate + choline orotate(molar ratio 1:2) | 124 mg/kg |

Also in this case, the clear superiority of the mixture sodium salicylate + choline orotate, quite particularly in the molar ratio of 1:2, was demonstrated.

EXAMPLE 6

As in Example 5, the $ED_{50}$ of metamizol and metamizol + choline orotate in the molar ratio of 1:2 was determined after one hour by the writhing test. The results are summarised in the following Table VI.

Table VI $ED_{50}$ in mg/kg of mouse 60 minutes after oral application.
Writhing test. 170 CFI mice (18 to 20 g).

|  | 60 mins. |
|---|---|
| Metamizol | 380 mg/kg |
| Metamizol + choline orotate (molar ratio 1:2) | 86 mg/kg |

This test, too, confirms the reinforcement of the analgesic efficacy of the metamizol by the addition of an orotic acid salt.

EXAMPLE 7

The analgesic effects of codeine phosphate and codeine phosphate + choline orotate (molar ratio 1:1) are compared in the writhing test on mice.

Table VII $ED_{50}$ in mg/kg of mouse. Writhing syndrome 60 minutes following oral application; 130 CFI mice, female, 20 to 22 g.

|  | 60 mins. |
| --- | --- |
| Codeine phosphate | 82 |
| Codeine phosphate + choline orotate (molar ratio 1:1) | 64 |
| Codeine phosphate + choline orotate (molar ratio 1:2) | 46 |

EXAMPLE 8

In all the foregoing examples (1 to 7), an increased amount of drug was found in the ultrafiltrate in the presence of orotic acid. On the other hand, in the presence of orotic acid, phenyl butazone was not found in increased quantity in the ultrafiltrate. Accordingly, also in animal experiments, there was no reinforced analgesia, as the following Table shows:

Table VIII $ED_{50}$ in mg/kg of mouse. Writhing syndrome 60 minutes following oral application; 90 CFI mice, female, 20 to 22 g.

|  | 60 mins. |
| --- | --- |
| Phenyl butazone | 130 ± 45 |
| Phenyl butazone + choline orotate (molar ratio 1:1) | 120 ± 60 |

The advantages of the invention reside particularly in that by the combination of the pharmacologically active substance with orotic acid, an orotic acid salt a considerable increase in effect is achieved. Where the therapeutic application is concerned, this allows a reduction of the necessary dosages. As the experiments also demonstrated, this applies to the usual types of application (enteral and parenteral).

The reinforcement of effect according to the invention can be demonstrated independently of the structure of the drugs used and can also be revealed for stereo isomers of varying pharmacological action.

With oral application, the increase in action is obviously dependent upon the resorption quotas of orotic acid or its salt.

We claim:

1. A method of treating a patient suffering from pain which comprises enterally or parenterally administering to said patient an enterally or parenterally administrable central nervous system effective analgesic composition selected from the group consisting of: (a) a composition comprising a central nervous system analgesic which exhibits in vivo and in vitro an affinity for blood proteins, and a member selected from the group consisting of orotic acid (1,2,3,6-tetrahydro-2,6-dioxo-4-pyrimidine-carboxylic acid), physiologically compatible orotic acid salts other than with said central nervous system analgesic, and mixtures thereof in an amount sufficient to increase the amount of said analgesic which is ultrafilterable from serum and to increase the analgesic efficiency of said analgesic; (b) composition comprising a physiologically compatible orotic acid salt of a central nervous system analgesic which exhibits in vivo and in vitro an affinity for blood proteins wherein the orotic acid moiety is in an amount sufficient to increase the amount of said analgesic which is ultrafilterable from serum and to increase the analgesic efficiency of said analgesic, and mixtures of (a) and (b).

2. The method of claim 1 wherein said member is orotic acid.

3. The method of claim 1 wherein said member is an orotic acid salt.

4. The method of claim 1 wherein the molar ratio of said member to said analgesic is at least 1:1.

5. The method of claim 1 wherein the molar ratio of said member to said analgesic is 2:1.

6. The method of claim 1 wherein said member is choline orotate.

7. The method of claim 1 which comprises administering a physiologically compatible orotic acid salt of said analgesic.

8. The method of claim 7 wherein said salt is orotic acid salt of dextropropoxyphene.

9. The method of claim 7 wherein said salt is a salt of codeine.

10. The method of claim 1 wherein said analgesic is sodium salicylate.

11. The method of claim 1 wherein said analgesic is metamizol.

12. The method of claim 1 wherein said analgesic is codeine.

13. The method of claim 7 which comprises administering a mixture of the orotic acid salt of the analgesic and another physiologically compatible orotic acid salt.

14. The method of claim 1 which comprises administering orotic acid and metamizol.

15. The method of claim 14 which contains orotic acid and metamizol.

16. An enterally or parenterally administrable central nervous system effective analgesic composition selected from the group consisting of: (a) a composition comprising a central nervous system analgesic which exhibits in vivo and in vitro an affinity for blood proteins, and a member selected from the group consisting of orotic acid (1,2,3,6-tetrahydro-2,6-dioxo-4-pyrimidine-carboxylic acid), physiologically compatible orotic acid salts other than with said central nervous system analgesic and mixtures thereof in an amount sufficient to increase the amount of said analgesic which is ultrafilterable from serum and to increase the analgesic efficiency of said analgesic; (b) composition comprising a physiologically compatible orotic acid salt of a central nervous system analgesic which exhibits in vivo and in vitro an affinity for blood proteins wherein the orotic acid moiety is in an amount sufficient to increase the amount of said analgesic which is ultrafilterable from serum and to increase the analgesic efficiency of said analgesic, and mixtures of (a) and (b).

17. The composition of claim 16 wherein said member is orotic acid.

18. The composition of claim 16 wherein said member is an orotic acid salt.

19. The composition of claim 16 wherein said analgesic is selected from the group consisting of sodium salicylate, codeine, metamizol, dextropropoxyphene, and mixtures thereof.

20. The composition of claim 16 wherein the molar ratio of said member to said analgesic is at least 1:1.

21. The composition of claim 16 wherein the molar ratio of said member to said analgesic is 2:1.

22. The composition of claim 16 wherein said member is choline orotate.

23. The composition of claim 16 which comprises a physiologically compatible orotic acid salt of said analgesic.

24. The composition of claim 23 wherein said salt is orotic acid salt of dextropropoxyphene.

25. The composition of claim 23 wherein said salt is a salt of codeine.

26. The composition of claim 16 wherein said analgesic is sodium salicylate.

27. The composition of claim 16 wherein said analgesic is metamizol.

28. The composition of claim 16 wherein said analgesic is codeine.

29. The composition of claim 16 which includes a mixture of the orotic acid salt of the analgesic and another physiologically compatible orotic acid salt.

30. The composition of claim 16 which contains orotic acid and sodium salicylate.

31. The composition of claim 16 which contains orotic acid and metamizol.

32. A method for increasing the analgesic efficiency of an enterally or parenterally administrable central nervous system effective analgesic composition selected from the group consisting of: (a) a composition containing a central nervous system analgesic which exhibits in vivo and in vitro an affinity for blood proteins which comprises adding to said analgesic a member selected from the group consisting of orotic acid (1,2,3,6-tetrahydro-2,6-dioxo-4-pyrimidine-carboxylic acid), physiologically compatible orotic acid salts other than with said central nervous system analgesic, and mixtures thereof in an amount sufficient to increase the amount of said analgesic which is ultrafilterable from serum and to increase the analgesic efficiency of said analgesic; (b) composition comprising a physiologically compatible orotic acid salt of a central nervous system analgesic which exhibits in vivo and in vitro an affinity for blood proteins wherein the orotic acid moiety is in an amount sufficient to increase the amount of said analgesic which is ultrafilterable from serum and to increase the analgesic efficiency of said analgesic, and mixtures of (a) and (b).

33. The method of claim 32 wherein said member is orotic acid.

34. The method of claim 32 wherein said member is an orotic acid salt.

35. The method of claim 32 wherein said analgesic is selected from the group consisting of sodium, salicylate, codeine, metamizol, dextropropoxyphene, and mixtures thereof.

36. The method of claim 32 wherein the molar ratio of said member to said analgesic is at least 1:1.

37. The method of claim 32 wherein the molar ratio of said member to said analgesic is 2:1.

38. The method of claim 32 wherein said member is choline orotate.

39. The method of claim 32 wherein said analgesic is sodium salicylate.

40. The method of claim 32 wherein said analgesic is metamizol.

41. The method of claim 32 wherein said analgesic is codeine.

* * * * *